United States Patent [19]
Hauser et al.

[11] Patent Number: 5,929,090
[45] Date of Patent: Jul. 27, 1999

[54] 2-ARYL-3-AMINOARYLOXYNAPHTHYl COMPOUNDS, INTERMEDIATES, COMPOSITIONS AND METHODS

[75] Inventors: Kenneth Lee Hauser, Greencastle; Alan David Palkowitz, Carmel, both of Ind.

[73] Assignee: Eli Lilly and Company, Indianapolis, Ind.

[21] Appl. No.: 08/928,305

[22] Filed: Sep. 12, 1997

[51] Int. Cl.$^6$ .................. A61K 31/445; C07D 295/08
[52] U.S. Cl. ............... 514/319; 514/212; 514/237.8; 514/238.2; 514/324; 540/609; 540/610; 544/165; 546/202; 546/205
[58] Field of Search ................. 546/202, 205; 540/609, 610; 564/165; 514/212, 237.8, 238.2, 319, 324

[56] References Cited

U.S. PATENT DOCUMENTS

| | | | |
|---|---|---|---|
| 3,274,213 | 9/1966 | Lednicer | 546/205 |
| 3,293,263 | 12/1966 | Lednicer | 546/205 |
| 3,313,853 | 4/1967 | Lednicer | 514/560 |
| 3,396,169 | 8/1968 | Lednicer | 546/205 |
| 3,483,293 | 12/1969 | Duncan et al. | 546/205 |
| 4,133,814 | 1/1979 | Jones et al. | 546/202 |
| 4,230,862 | 10/1980 | Swarez et al. | 546/237 |
| 4,380,635 | 4/1983 | Peters | 546/202 |
| 4,418,068 | 11/1983 | Jones | 546/202 |
| 4,910,212 | 3/1990 | Boyle et al. | 514/383 |
| 5,013,761 | 5/1991 | Beedle et al. | 514/650 |
| 5,254,568 | 10/1993 | Kapil et al. | 514/320 |

FOREIGN PATENT DOCUMENTS

| | | |
|---|---|---|
| 0062503 | 10/1982 | European Pat. Off. |
| 0124369 | 11/1984 | European Pat. Off. |
| 0703228 | 3/1996 | European Pat. Off. |
| 0729951 | 9/1996 | European Pat. Off. |
| 0731093 | 9/1996 | European Pat. Off. |
| 0733620 | 9/1996 | European Pat. Off. |
| WO 93/10741 | 6/1993 | WIPO |
| WO 95/10513 | 4/1995 | WIPO |
| WO 97/04763 | 2/1997 | WIPO |

OTHER PUBLICATIONS

Durani, N., et al., *Indian J. Chem.*, 22B:489–490 (1983).
Jones, C.D., et al., *J. Med. Chem.*, 35:931–938 (1992).
Lednicer, D., et al., *J. Med. Chem.*, 8:52–57 (1964).
Lednicer, D., et al., *J. Med. Chem.*, 9:172–175 (1965).
Lednicer, D., et al., *J. Med. Chem.*, 10:78–84 (1967).
Oparil "Hypertension in postmenopausal women . . . " EMBASE 9523951, 1995.
Insua et al. "Postmenopause, plasma lipoproteins and hormone replacement therapy", 1993.
Fuchs Young et al. "Inhibition of estroten stimulated growth of uterine leiomyomas by SERM" Mol. Carcinogen. 17, 151–159, 1996.
Haber et al. "Preliminary report on the use of tamoxifen in the treatment of endometriosis" Am. J. Ob. Gyn. 156, 582–586, 1987.

*Primary Examiner*—Ceila Chang
*Attorney, Agent, or Firm*—Gilbert T. Voy

[57] ABSTRACT

The present invention provides a compound of formula I:

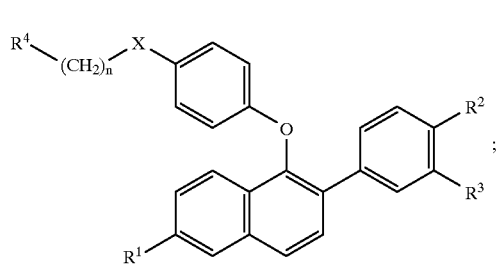

or a pharmaceutically acceptable salt or solvate thereof; having activity as a selective estrogen receptor modulator, pharmaceutical compositions containing a compound of formula I, and methods of using a compound of formula I for treating conditions resulting from estrogen deprivation or the inappropriately high presence of estrogen. Also provided are methods and chemical intermediates for the production of a compound of formula I above.

24 Claims, No Drawings

2-ARYL-3-AMINOARYLOXYNAPHTHY1 COMPOUNDS, INTERMEDIATES, COMPOSITIONS AND METHODS

FIELD OF THE INVENTION

This invention relates to organic compounds having biological activity, to compositions containing the compounds and methods for their preparation and use. More particularly, in its principal aspect, the present invention concerns a class of substituted naphthyl compounds having activity as selective estrogen receptor modulators, to pharmaceutical compositions containing those compounds, and to a method of treating conditions associated with inappropriate levels of estrogen and the attendant pathological sequelae, inter alia, post-menopausal syndrome, osteoporosis, cardiovascular disease, estrogen dependent cancer, uterine fibroid disease, endometriosis, and aortal smooth muscle cell proliferation.

The present invention further relates to processes and intermediate compounds useful for preparing the pharmaceutically active compounds of the principal aspect of the present invention.

BACKGROUND OF THE INVENTION

Estrogen is a generic term for estrus-producing steroid compounds. Within the "estrogen group" are the traditional steroids such as 17β-estradiol and estrone (the major estrogens in humans), as well as various metabolites such as the estratriols, sulfates and glucuronides of estradiol and estrone. Also, germane to human medicine, are the steroidal equine estrogens such as the equilins, in that they are administered to humans in preparations, such as Premarin™. Also, certain compounds known as "anti-estrogens", e.g., tamoxifen, clomiphene, nafoxidene, and raloxifene, demonstrate varying degrees of estrogen agonist properties in some tissues; however they act to antagonize the natural estrogens and their function in other tissues.

Recently, these "anti-estrogens" have been categorized into three different types depending on their degree and mix of estrogen agonist/antagonist properties which is based on their ability to freeze estrogen receptors in different conformational states, cf. D. P. McDonnell, et al., *Molecular Endocrinology*, 9(6): 659–669 (1995). Most germane are the type II anti-estrogens of which compounds of the current invention belong. The chemical structures of these various anti-estrogen types, although often similar, are poor predictors of pharmacological activity, in that small chemical changes produce varied activity.

Estrogens as biologically active molecules exert their properties by binding to an intracellular receptor. After the receptor and bound ligand are transported to the nucleus of a cell, the complex exerts its effect by binding to certain recognition sites on DNA and allowing certain genes to be expressed. This binding to the receptor and regulation is poorly understood; however, it appears to be crucial to the varying agonist and antagonist properties of the anti-estrogens. Thus, certain types of anti-estrogens allow agonist activity in some tissues, but are antagonists in others. Hence, the term, "selective estrogen receptor modulators (SERMs)" has been proposed to describe these molecules, especially the type II, of which the compounds of the current invention are members.

Estrogen has long been classified as "the female sex hormone" and a voluminous literature describes its activity as such. However, in recent years, research has shown that estrogens have many other homeostatic functions, other than those related to female reproduction and function of sex tissues. Indeed, it has been shown that males possess estrogen receptors and DNA recognition sites and possess the ability to produce estrogens and many tissues, such as those involved in the cardiovascular system. The exact nature of the effects of estrogens in both men and women, outside the productive aspects, are only beginning to be explored and are currently poorly understood.

The majority of the documented activities of the estrogens have been derived from studies in women, since most women suffer from the most obvious effects of estrogen, mainly due to menopause and estrogen dependent cancers. The clinical pathologies associated with estrogen levels and their subsequent function, can be categorized into two main types, i.e., those which are due to a deprivation or lack of estrogen and those which are due to an aberrant physiological response to existing estrogen in estrogen sensitive tissues. SERMS, especially those of the current invention, have the property of being estrogen agonists in those cases where estrogen deprivation is a cause of pathology (mainly in non-sex related tissues) and simultaneously being antagonists of the pathologies caused by abnormal responses to endogenous estrogen (in sex related tissues).

Thus, SERMS of the type II class (compounds of formula I) have the potential to effectively treat a variety of estrogen dependent pathological conditions. This dual effect is an intrinsic and unique property of the molecules of the present invention.

SUMMARY OF THE INVENTION

The present invention provides, in its principal aspect, a compound of formula I

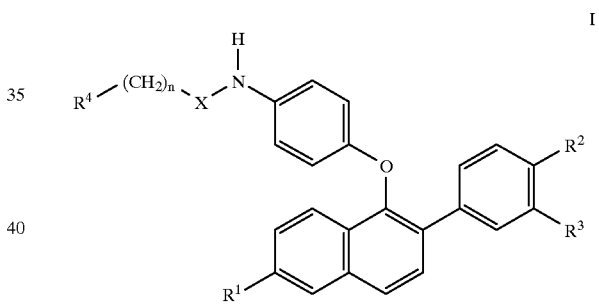

or a pharmaceutically acceptable salt thereof wherein n is 1, 2 or 3.

The substituent group $R^1$ is selected from the group consisting of hydrogen, hydroxyl, alkoxy of one to four carbon atoms, alkoxycarbonyl of two to seven carbon atoms, —$OSO_2$($C_1$–$C_6$ alkyl), and —OCOAr where Ar is selected from the group consisting of unsubstituted phenyl, and phenyl substituted with one or more substituents independently selected from the group consisting of halo, nitro, trifluoromethyl, methyl, and methoxy.

$R^2$ and $R^3$ are independently selected from the group consisting of hydrogen, hydroxyl, halo, alkoxy of one to four carbon atoms, alkoxycarbonyl of two to seven carbon atoms, —$OSO_2$($C_2$–$C_6$ alkyl), and —OCOAr where Ar is selected from the group consisting of unsubstituted phenyl and phenyl substituted with one or more substituents independently selected from the group consisting of halo, nitro, trifluoromethyl, methyl, and methoxy.

The substituent $R^4$ is selected from the group consisting of 1-piperidinyl, 1-pyrrolidinyl, methyl-1-pyrrolidinyl, dimethyl-1-pyrrolidino, 4-morpholino, dimethylamino, diethylamino, diisopropylamino, and 1-hexamethyleneimino.

X is absent or is selected from the group consisting of —C(O)— and —SO$_2$—.

In a second embodiment, the invention provides compounds which are novel and useful intermediates for preparing the pharmaceutically active compounds of the present invention, which intermediates have the structure of formula II:

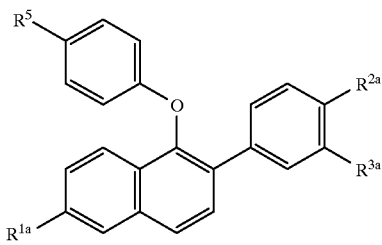

or a pharmaceutically acceptable salt or solvate thereof.

$R^{1a}$ is selected from the group consisting of hydrogen, and —OR$^6$ in which R$^6$ is a hydroxy protecting group.

$R^{2a}$ and $R^{3a}$ are independently selected from the group consisting of hydrogen, halo, and —OR$^6$ where R$^6$ is defined above.

R$^5$ is selected from the group consisting of —NO$_2$, —NH$_2$, and Y—(CH$_2$)$_n$—X$^a$—NH— where Y is chloro or bromo; and X$^a$ is —CO— or —SO$_2$—.

In yet another embodiment, the present invention provides a pharmaceutical composition comprising a therapeutically effective amount of a compound of formula I, alone or in combination with estrogen or progestin, and a pharmaceutically acceptable carrier.

In a further embodiment, the present invention provides a medical method of employing compounds of the present invention, for alleviating the symptoms of estrogen deprivation, including post-menopausal syndrome, osteoporosis, hypertension and thrombosis.

In an alternative embodiment of the medical method of the present invention, the compounds of the present invention are employed in the treatment of disease conditions associated with an aberrant physiological response to endoqenous estrogen including uterine fibroid disease or uterine fibrosis, endometriosis in women, and estrogen dependent cancers in humans.

DETAILED DESCRIPTION OF THE INVENTION

Throughout this specification and the appended claims, the following terms have the definitions and usages ascribed to them below.

"$C_1$–$C_6$ alkyl" refers to monovalent groups derived by the removal of one hydrogen atom from methane or straight or branched aliphatic hydrocarbons of 2 to 6 carbon atoms and includes groups such as methyl, ethyl, propyl, isopropyl, butyl, n-butyl, pentyl, isopentyl, hexyl, isohexyl, and the like.

Similarly, the term "O—($C_1$–$C_6$ alkyl)," "alkoxy" or "alkoxyl" represents a $C_1$–$C_6$ alkyl group as defined above attached to the parent molecular moiety through an oxygen molecule and include groups such as methoxy, ethoxy, n-propoxy, isopropoxy, and the like. Of these alkoxy groups, methoxy is most preferred.

The term "alkoxycarbonyl" denotes an alkoxy group, as defined above, connected to the parent molecular moiety through a carbonyl group and is typified by such groups as methoxycarbonyl, ethoxycarbonyl, propoxycarbonyl and the like.

The term "solvate" represents an aggregate that comprises one or more molecules of the solute, such as a formula I compound, with one or more molecules of solvent.

The term "estrogen" denotes steroidal compounds having estrogenic activity such as, for example, 17b-estradiol, estrone, conjugated estrogen (Premarin®), equine estrogen 17b-ethynyl estradiol, and the like. As used herein, the term "progestin" includes compounds having progestational activity such as, for example, progesterone, norethylnodrel, nongestrel, megestrol acetate, norethindrone, and the like.

The term, "estrogen deprivation" is meant to imply the condition where the optimal level of estrogen is absent. This level varies from one tissue to another depending on the function of the tissue. Thus, in some cases, estrogen deprivation may be the total absence of estrogen, where as in other cases, deprivation may involve estrogen levels which are too low for proper tissue function. In women, the two most common causes of estrogen deprivation are menopause and ovariectomy, although other conditions can be causative.

In women, the failure of the ovaries to produce adequate levels of estrogen, regardless of cause, leads to a condition generally described as post-menopausal syndrome. "Post-menopausal syndrome" as used throughout this specification and the appended claims describes the pathological conditions which frequently affect women who have entered into or completed the physiological metamorphosis known as menopause. Although numerous pathologies are contemplated by the use of this term, two major effects of post-menopausal syndrome are the source of the greatest long-term medical concern: osteoporosis and cardiovascular effects such as hyperlipidemia, proliferation of aortal smooth muscle cells (restenosis), decrease in nitric oxide production (hypertension) and decrease in production of the enzyme PAI-1 (Plasminogen Activator Inhibitor-1), i.e. thrombosis.

Specific examples of compounds contemplated as falling within the scope of the present invention include, but are not limited to:

1-[4-[2-(1-piperidinyl)ethylamino]phenoxy]-2-(4-hydroxyphenyl)-6-hydroxynaphthalene;
1-[4-[2-(1-piperidinyl)ethylamino]phenoxy]-2-(4-methoxyphenyl)-6-methoxynaphthalene;
1-[4-[2-(1-piperidinyl)ethylamino]phenoxy]-2-(4-hydroxyphenyl)-6-methoxynaphthalene;
1-[4-[2-(1-piperidinyl)ethylamino]phenoxy]-2-(4-methoxyphenyl)-6-hydroxynaphthalene;
1-[4-[2-(1-pyrolidinyl)ethylamino]phenoxy]-2-(4-hydroxyphenyl)-6-hydroxynaphthalene;
1-[4-[3-(1-piperidinyl)propylamino]phenoxy]-2-(4-hydroxyphenyl)-6-hydroxynaphthalene;
1-[4-[2-(1-piperidinyl)ethylamino]phenoxy]-2-(3-hydroxyphenyl)-6-hydroxynaphthalene;
1-[4-[2-(1-piperidinyl)ethylamino]phenoxy]-2-(3-methoxyphenyl)-6-hydroxynaphthalene;
1-[4-[2-(1-piperidinyl)ethylamino]phenoxy]-2-(4-hydroxyphenyl)naphthalene;
1-[4-[2-(1-piperidinyl)ethylamino]phenoxy]-2-(4-methoxyphenyl)naphthalene;
1-[4-[2-(1-piperidinyl)ethylamino]phenoxy]-2-(3-hydroxyphenyl)naphthalene;
1-[4-[2-(1-piperidinyl)ethylamino]phenoxy]-2-(3-methoxyphenylnaphthalene;
1-[4-[2-(1-piperidinyl)ethylamino]phenoxy]-2-(4-acetyloxyphenyl)-6-hydroxynaphthalene;
1-[4-[2-(1-piperidinyl)ethylamino]phenoxy]-2-(4-hydroxyphenyl)-6-benzoyloxynaphthalene;

1-[4-[2-(1-piperidinyl)acetylamido]phenoxy]-2-(4-hydroxyphenyl)-6-hydroxynaphthalene;

1-[4-[2-(1-pyrolidinyl)acetylamido]phenoxy]-2-(4-hydroxyphenyl)-6-hydroxynaphthalene;

1-[4-[2-(1-piperidinyl)acetylamido]phenoxy]-2-(4-methoxyphenyl)-6-methoxynaphthalene;

1-[4-[2-(1-piperidinyl)acetylamido]phenoxy]-2-(3-hydroxyphenyl)-6-hydroxynaphthalene;

1-[4-[2-(1-piperidinyl)acetylamido]phenoxy]-2-(4-hydroxyphenyl)naphthalene;

1-[4-[2-(1-piperidinyl)acetylamido]phenoxy]-2-(4-methoxyphenyl)-6-hydroxynaphthalene;

1-[4-[3-(1-piperidinyl)propanoylamido]phenoxy]-2-(4-hydroxyphenyl)-6-hydroxynaphthalene;

1-[4-[(1-piperidinyl)methylsulfonoylamido]phenoxy]-2-(4-hydroxyphenyl)-6-hydroxynaphthalene; and 1-[4-[2-(1-piperidinyl)ethylsulfonoylamido]phenoxy]-2-(4-hydroxyphenyl)-6-hydroxynaphthalene.

Preferred compounds in accordance with the present invention include, but are

1-[4-[2-(1-piperidinyl)ethylamino]phenoxy]-2-(4-hydroxyphenyl)-6-hydroxynaphthalene; or a pharmaceutically acceptable salt thereof; and 1-[4-[2-(1-piperidinyl)acetylamido]-phenoxy]-2-(4-hydroxyphenyl)-6-hydroxynaphthalene or a pharmaceutically acceptable salt thereof, particularly the hydrochloride salt.

The compounds of the present invention are useful in the treatment of conditions associated with estrogen deprivation in women which can result from either ovariectomy or from the natural decrease in estrogen levels following menopause. Estrogen deprivation can lead to conditions including osteoporosis and cardiovascular effects such as hyperlipidemia, proliferation of aortal smooth muscle cells (restenosis), decrease in nitric oxide production (hypertension) and decrease in production of the enzyme PAI-1 (Plasminogen Activator Inhibitor-1), i.e. thrombosis.

Osteoporosis describes a group of diseases which arise from diverse etiologies, but which are characterized by the net loss of bone mass. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. Osteoporosis is a common and serious disease among post-menopausal women. There are an estimated 25 million women in the United States, alone, who are afflicted with this disease. The results of osteoporosis are personally harmful and also account for a large economic loss due its chronicity and the need for extensive and long term support (hospitalization and nursing home care) from the disease. At this time, the most predominate method for treatment of post-menopausal osteoporosis is estrogen replacement therapy. Although this therapy is generally successful, patient compliance with the therapy is low primarily because estrogen treatment frequently produces undesirable side effects, especially on uterine and breast tissue. Recently, a new treatment for post-menopausal osteoporosis has been advanced, i.e., treatment with bis-phosphonates. Although this therapy is effective, it suffers the disadvantage of only treating the osteoporosis aspect of the post-menopausal syndrome.

In the case of post-menopausal cardiovascular problems in women, it has long been known that throughout pre-menopausal time most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. It has been reported in the literature that post-menopausal women having estrogen replacement therapy have a return of cardiovascular protection similar to those of the pre-menopausal state. Thus, estrogen would appear to be a reasonable treatment for this condition. However, the side-effects of estrogen replacement therapy are not acceptable to many women, thus limiting the use of this therapy.

Reduction or amelioration of other pathologies associated with menopause such as urinary incontinence, vaginal dryness, increase in the incidence of auto-immune disease, loss of skin tone, vasomotor complications (hot flashes), and psychological problems, also have been ascribed to estrogen replacement therapy.

In addition to their usefulness in treating conditions associated with estrogen deprivation following menopause, the compounds of the present invention are also useful in the treatment of disease states associated with inappropriate response to endogenous estrogen in tissues both prior to and subsequent to menopause.

One example of a pathological condition associated with abnormal cellular responses to endogenous estrogen in tissues is estrogen dependent breast cancer. Estrogen dependent breast tumor cells proliferate in the presence of estrogen and the treatment of this disease has been to stop all action of estrogen on these cells. Current chemotherapy of these cancers has relied heavily on the use of anti-estrogen compounds of type I (McDonnell, et al. see above), e.g., tamoxifen. Although such mixed agonist-antagonists have beneficial effects in the treatment of these cancers and the estrogenic side-effects are tolerable in acute life-threatening situations, their use is not ideal. For example, these agents often have stimulatory effects on certain cancer cell populations in the uterus due to their estrogenic (agonist) properties and they may, therefore, be counterproductive in some cases in the treatment of breast cancer. A better therapy for the treatment of these cancers are agents which are anti-estrogen compound having negligible or no estrogen agonist properties on primary sex tissues.

Another estrogen dependent pathology is uterine fibrosis (uterine fibroid disease). Essentially, uterine fibrosis is a condition where there is a deposition of fibroid tissue on the wall of the uterus. This condition is a cause of dysmenorrhea and infertility in women. The exact cause of this condition is poorly understood but evidence suggests that it is an inappropriate response of fibroid tissue to estrogen. The most common treatment of uterine fibrosis involves surgical procedures both costly and sometimes a source of complications such as the formation of abdominal adhesions and infections.

Yet another disease in this category is endometriosis, a condition of severe dysmenorrhea, which is accompanied by severe pain, bleeding into the endometrial masses or peritoneal cavity and often leads to infertility. The cause of the symptoms of this condition appear to be ectopic endometrial growths located in inappropriate tissues which respond inappropriately to hormonal control.

The present invention also provides a method of alleviating estrogen deprivation in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Administration

As used herein, the term "effective amount" or "therapeutically effective amount" means an amount of compound of the present invention which is capable of alleviating, in whole or in part, the symptoms of the various pathological conditions herein described. The specific dose of a compound administered according to this invention will, of course, be determined by the particular circumstances surrounding the case including, for example, the potency of the compound administered, the route of administration, the prior medical history of the patient, and the severity of the condition being treated. However, it is within the skill of the art to "titrate" the patient for the correct dose; that is, to initially administer a dose of the compound which is insufficient to produce the desired effect, and to gradually increase the dose until the desired effect is achieved.

A typical daily dose will contain a nontoxic dosage level of from about 5 mg to about 600 mg/day of a compound of the present invention. Preferred daily doses generally will be from about 15 mg to about 80 mg/day.

In combination therapy with estrogen or progestin, the compounds of the present invention are administered to a patient, either with a separate dosage form of estrogen or progestin or in a single dosage form which contains a compound of the present invention together with a therapeutically effective amount of either or both estrogen or progestin.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

Test Procedure

General Preparation Procedure

In the examples illustrating the methods, an estrogen deprivation model was used in which effects of different treatments upon circulating lipids were determined.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection. After a one week acclimation period (therefore, two weeks post-OVX) daily dosing with test compound is initiated. 17a-ethynyl estradiol or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis. Blood samples are allowed to clot at ambient temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one with hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay. Uteri are kept at 4° C. until time of enzymatic analysis. The uteri are then homogenized in 50 volumes of 50 mM Tris buffer (pH –8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosinophils in the uterus is an indication of estrogenic activity of a compound. The maximal velocity of a 15 second interval is determined over the initial, linear portion of the reaction curve.

Source of Compound: 17a-ethynyl estradiol was obtained from Sigma Chemical Co., St. Louis, Mo.

Selected compounds of formula I were evaluated in the above assay. These results are presented in Table 1.

TABLE 1

| Example | Dose (mg/kg)[a] | Uterine Weight (% Inc.)[b] | Uterine Eosinophil $(V_{max})$[c] | Serum Cholesterol (% Dec.)[d] |
|---|---|---|---|---|
| EE2[e] | 0.1 | 96.0* | 54.6* | 75.9* |
| 2 | 0.1 | 13.6 | 1.8 | 27 |
|  | 1.0 | 59.0* | 11.7 | 66.4* |
|  | 10.0 | 107.0* | 71.1* | 57.6* |
| 4 | 0.01 | 7.1 | 2.7 | 20.8* |
|  | 0.1 | 39.8* | 4.5 | 59.9* |
|  | 1.0 | 25.4 | 5.4 | 75.3* |

[a]mg/kg PO
[b]Uterine Weight % increase versus the ovarierectomized controls
[c]Eosinophil peroxidase Vmaxium
[d]Serum cholesterol decrease versus ovariectomized controls
[e]17-a-Ethynyl-estradiol
*p < .05

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl b-cyclodextrin are orally administered to test animals.

A model illustrating the utility of the compounds of formula I, where the undesired pathology is due to an inappropriate presence of estrogen, is shown, below.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 mL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 mL transferred to triplicate microcultures followed by 50 mL assay medium for a final volume of 200 mL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace b counter. Activity of a compound of formula I in the present assay demonstrates that the compound is of potential for treating hormonally-dependent cancer, particularly breast cancer.

DMBA-Induced Mammary Tumor Inhibition

Estrogen-dependent mammary tumors are produced in female Sprague-Dawley rats which are purchased from Harlan Industries, Indianapolis, Indiana. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Activity in the above tests indicates that the compounds of the present invention are of potential use in the treatment of restenosis.

Pharmaceutical Formulations

The present invention also provides pharmaceutical compositions which comprise compounds of the present invention formulated together with one or more non-toxic pharmaceutically acceptable carriers and/or excipients. The formulations may be specially formulated for oral administration, in solid or liquid form, for parenteral injection, or for rectal or vaginal administration by means of a suppository.

The pharmaceutical compositions of this invention can be administered to humans and other mammals orally, rectally, intravaginally, parenterally, topically (by means of powders, ointments, creams, or drops), bucally or sublingually, or as an oral or nasal spray. The term "parenteral administration" refers herein to modes of administration which include intravenous, intramuscular, intraperitoneal, instrasternal, subcutaneous, or intraarticular injection or infusion.

Pharmaceutical compositions of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral compositions may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Prolonged absorption of injectable formulations may be brought about by the inclusion of agents which delay absorption such as aluminum monostearate and gelatin.

In some cases, in order to prolong the effect of the drug, it is desirable to slow the absorption of the drug following subcutaneous or intramuscular injection. This may be accomplished by the use of a liquid suspension or crystalline or amorphous material of low water solubility or by dissolving or suspending the drug in an oil vehicle. In the case of the subcutaneous or intramuscular injection of a suspension containing a form of the drug with low water solubility, the rate of absorption of the drug depends upon its rate of dissolution.

Injectable "depot" formulations of the compounds of this invention are made by forming microencapsulated matrices of the drug in biodegradable polymers such as poly(lactic acid), poly(glycolic acid), copolymers of lactic and glycolic acid, poly (orthoesters), and poly (anhydrides) these materials which are described in the art. Depending upon the ratio of drug to polymer and the characteristics of the particular polymer employed, the rate of drug release can be controlled.

Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, the active component is mixed with at least one inert, pharmaceutically acceptable carrier such as sodium citrate, or dicalcium phosphate, and/or (a) fillers or extenders such as starches, lactose, glucose, mannitol, and silicic acid, (b) binding agents such as carboxymethylcellulose, alginates, gelatin, poly(vinylpyrrolidine), sucrose and acacia, (c) humectants such as glycerol, (d) disintegrating agents such as agar-agar, calcium carbonate, potato or tapioca starch, alginic acid, silicates and sodium carbonate, (e) solution retarding agents such as paraffin, (f) absorption accelerating agents such as quaternary ammonium compounds, (g) wetting agents such as cetyl alcohol and glycerin monostearate, (h) absorbents such as kaolin and bentonite clay, and (i) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid compositions of a similar type may also comprise the fill in soft or hard gelatin capsules using excipients such as lactose as well as high molecular weight poly(ethylene glycols) and the like.

Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract.

The active ingredient(s) may also be microencapsulated in a sustained-release coating, with the microcapsules being made part of a pill of capsule formulation.

Liquid dosage forms for oral administration of the compounds of this invention include solution, emulsions, suspensions, syrups and elixirs. In addition to the active components, liquid formulations may include inert diluents commonly used in the art such as water or other pharmaceutically acceptable solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof.

Besides inert diluents, the liquid oral formulations may also include adjuvants such as wetting agents, emulsifying and suspending agents, and sweetening, flavoring, and perfuming agents.

Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Compositions for rectal or intravaginal administration are prepared by mixing one or more compounds of the present invention with suitable non-irritating excipients such as cocoa butter, polyethylene glycol or any suppository wax which is a solid at room temperature, but liquid at body temperature and therefore melt in the rectum or vaginal cavity to release the active component(s). The compounds are dissolved in the melted wax, formed into the desired shape, and allowed to harden into the finished suppository formulation.

Compounds of the present invention may also be administered in the form of liposomes. As is know in the art, liposomes are generally derived from phospholipids or other lipid substances. Liposome formulations are formed by mono- or multilamellar hydrated liquid crystals which are dispersed in an aqueous medium. Any non-toxic, pharmaceutically acceptable, and metabolizable lipid capable of forming liposomes can be used. The present compositions in liposome form can contain, in addition to one or more active compounds of the present invention, stabilizers, excipients, preservatives, and the like. The preferred lipids are phospholipids and the phosphatidyl cholines (lecithins), both natural and synthetic.

Methods for forming liposomes are know in the art as described, for example, in Prescott, Ed., *Methods in Cell Biology*, Volume XIV, Academic Press, New York, N.Y. (1976), p. 33 et seq.

Dosage forms for topical administration of the compounds of the present invention include powders, sprays, ointments, creams, and inhalants. The active ingredient(s) is mixed under sterile conditions with a suitable pharmaceutically acceptable carrier and preservatives, buffers, or propellants as needed. Opthalmic formulations, eye ointments, and solutions are also contemplated as falling within the scope of the present invention.

Actual dosage levels of compounds of the present invention are varied so as to administer an amount of the compound which is effective to bring about the desired therapeutic affect. The dose required for a given patient will vary depending upon the severity of the condition being treated, the age, weight, and sex of the patient, as well as the state of health of the patient. However, it is within the skill of the art to "dose titrate" the patient; that is, to begin administering a dose known to be below the amount required to bring about the desired therapeutic effect and to gradually increase the dose until the desired effect is achieved.

Generally, for the treatment of estrogen-related disorders, compounds of the present invention are administered at dosage levels between about 10 mg/kg of body weight and about 250 mg/kg of body weight per day. If desired, the daily dosage may be divided into multiple doses for purposes of administration, e.g. into two to four doses per day.

The following examples of pharmaceutical formulations are provided to enable one skilled in the art to practice the present invention and are not to be read as limiting the scope of the invention as it is defined by the appended claims.

In the formulations which follow, "active ingredient" means a compound of formula I, or a salt or solvate thereof.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 4: Suspensions

| Ingredient | Quantity (mg/5 mL) |
| --- | --- |
| Active ingredient | 0.1–1000 mg |
| Sodium carboxymethyl cellulose | 50 mg |
| Syrup | 1.25 mg |
| Benzoic acid solution | 0.10 mL |

-continued

| Ingredient | Quantity (mg/5 mL) |
| --- | --- |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol Formulation

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppository Formulation

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 | wherein $R^{1a}$ is —H or —$OR^6$ in which $R^6$ is a hydroxy protecting group; and $R^{2a}$ and $R^{3a}$ are, independently, —H, —F, —Cl, or —$OR^7$ in which $R^7$ is a hydroxy protecting group.

Compounds of formula III are well known in the art and are prepared essentially as described by Boyle, et al., in U.S. Pat. No. 4,910,212 which is incorporated herein by reference. See., also, Collins, D. J., et al., *Aust. J. Chem.*, 41:745–756 (1988); and Collins, D. J., et al., *Aust. J. Chem.*, 37:2279–2294 (1984).

In preparing compounds of the present invention, generally, a ketone of formula III is aromatized, providing a phenol of formula IV, which is then reacted with a 4-nitro-1-fluorobenzene to give a biaryl ether of formula IIa, which, in turn, is reduced to a amine of formula IIb. This synthetic route is as shown below in Scheme I, and $R^{1a}$, $R^{2a}$, and $R^{3a}$ are as defined above.

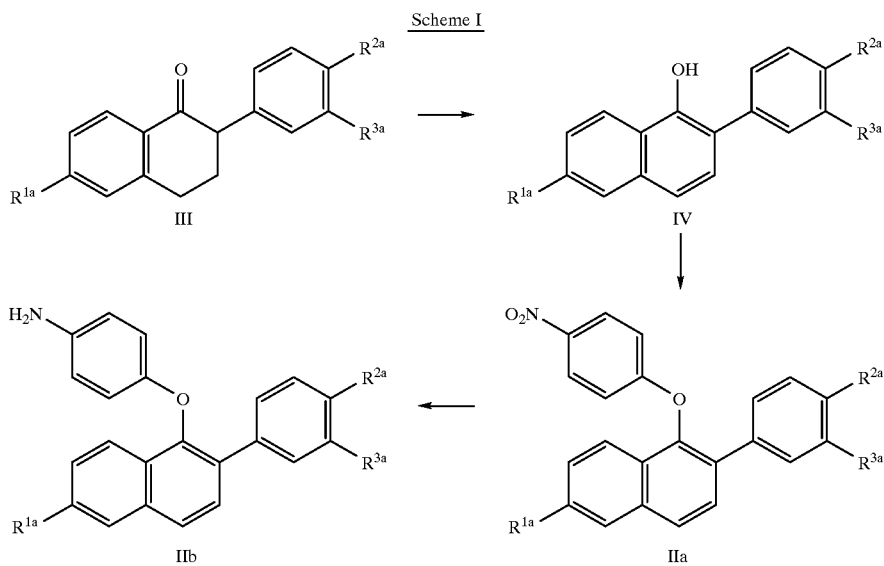

Preparation of Compounds of the Invention

The starting material for preparing compounds of the present invention is a compound of formula III

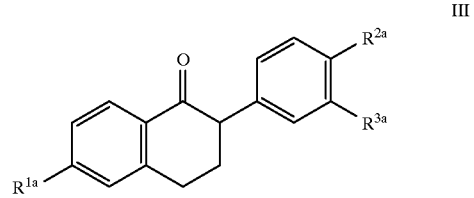

In the first step of the present process, a compound of formula III is converted to a phenol of formula IV via a three-step protocol, essentially as described by Wang, G., et al., *M. Syn. Commun.*, 21:989 (1991). In essence, a formula III ketone is enolized by refluxing with an acylating agent in an appropriate solvent, in the presence of an acid catalyst. The resulting enol acetate is directly converted to a naphthol acetate which is then hydrolyzed to a phenol of formula IV.

In converting a ketone of formula III to its respective enol, various known acid catalysts can be used. Preferably, non-aqueous acids, and particularly, p-toluenesulfonic acid is preferred.

Appropriate acylating agents include, for example, simple enol esters of acetate acid, particularly isopropenyl acetate, which serves as the solvent.

When run at reflux, the present reaction takes from about 6 to about 48 hours to complete. The enol product from this reaction is not isolated, but upon completion of the reaction, the resulting solution is treated with an appropriate oxidant and heated to reflux for, optimally, about 1 to about 3 hours.

Appropriate oxidants for this second phase of the first reaction step shown in Scheme I are limited to those known in the art which can lead to the elimination of a hydrogen atom from a saturated system to give an aromatized system. Such oxidants include, for example, hydrogenation catalysts such as platinum, palladium, and nickel, elemental sulfur and selenium, and quinones. For the present application, quinone oxidants, especially 2,3-dichloro-5,6-dicyano-1,4-benzoquinone (DDQ) are preferred. About 1 to 2 equivalents of DDQ per equivalent of substrate will drive the present process phase.

The resulting product of the present phase, a naphthol acetate, is then subjected to hydrolysis to provide a compound of formula IV, thus completing the first process step shown above in Scheme I. The present hydrolysis phase is accomplished via either acid or basic hydrolysis of the substrate in a polar protic solvent such as water or one or more solvents containing an alcohol such as methanol or ethanol. A cosolvent such as tetrahydrofuran (THF) or dioxane also may be added to the solution to aid solubility. Appropriate bases for this phase include sodium hydroxide, potassium hydroxide, lithium hydroxide, and the like. Appropriate acids include, for example, hydrochloric acid, methanesulfonic acid, p-toluenesulfonic acid, and the like.

This final phase of the first step shown in Scheme I above can be run at ambient temperature and runs in a short period of time, typically from 1 to about 12 hours. Completion of the present reaction can be determined via standard chromatographic techniques such as thin layer chromatography.

In the second step of the process depicted in Scheme I, a phenol of formula IV is first reacted with a base, followed by the addition of a 4-nitro-1-fluorobenzene in a polar aprotic solvent, under an inert atmosphere such as nitrogen, to give a biaryl ether of formula IIa. This reaction is well known in the art and is carried out essentially as described by Yeager, G. W., et al., *Synthesis*, 63 (1991). More particularly, 1 equivalent of a formula IV compound is first treated with at least 1 equivalent of a strong base, such as, an alkali metal hydride, alkoxide, or carbonate in an appropriate solvent, followed by a dropwise addition of a 4-nitro-1-fluorobenzene in the same solvent as used with the substrate.

Appropriate solvents for this reaction are those solvents or mixture of solvents which remain inert throughout the reaction. N,N-dimethylformamide (DMF), especially the anhydrous form thereof, is preferred. The preferred base for this reaction step, is potassium t-butoxide.

The temperature employed in this step of the present process should be sufficient to effect completion of this reaction, without encouraging the formation of undesirable by-products. A preferred temperature range for this reaction is from about 30° C. to about 100° C. Under preferred reaction conditions, a formula IIa compound will be prepared via the preferred process in about 24 to about 48 hours.

The final reaction step in Scheme I is the reduction of the nitro group to the corresponding amine. A variety of methods may be used to bring about this conversion. Among such methods would be the use of metal hydrides, such as $LiAlH_4$ and the like, in inert solvents such as THF or other nitro reducing agent such as sodium dithionite. Also, catalytic hydrogenations can be used, employing catalysts such as, palladium, platinum, or nickel. Preferred in this case, was the use of 5% palladium on a carbon substrate, in a solvent of EtOH/EtOAc.

Compounds of formula IIa and IIb are useful intermediate compounds which are useful for the preparation of pharmaceutically active compounds of formula I of the present invention.

Novel and useful intermediates of formula II include, but are not be limited to:

1-(4-aminophenoxy)-2-(3-methoxyphenyl)-6-methoxynaphthalene;

1-(4-aminophenoxy)-2-(3,4-dimethoxyphenyl)-6-methoxynaphthalene;

1-(4-nitrophenoxy)-2-(3-methoxyphenyl)-6-methoxynaphthalene;

1-(4-aminophenoxy)-2-(3-methoxyphenyl)naphthalene;

1-(4-aminophenoxy)-2-(3-fluoro-4-methoxyphenyl)-6-methoxynaphthalene;

1-(4-aminophenoxy)-2-(3,4-dimethoxyphenyl)naphthalene;

1-(4-nitrophenoxy)-2-(3-fluoro-4-methoxyphenyl)-6-methoxynaphthalene;

1-(4-nitrophenoxy)-2-(3,4-dimethoxyphenyl)naphthalene;

1-(4-nitrophenoxy)-2-(3-methoxyphenyl)naphthalene;

1-(4-nitrophenoxy)-2-(3-chlorophenyl)-6-methoxynaphthalene;

1-(4-aminophenoxy)-2-(3-chlorophenyl)-6-methoxynaphthalene;

1-(4-nitrophenoxy)-2-(3-chloro-4-methoxyphenyl)-6-methoxynaphthalene;

1-(4-aminophenoxy)-2-(3-chloro-4-methoxyphenyl)-6-methoxynaphthalene;

1-(4-aminophenoxy)-2-(3-chloro-4-methoxyphenyl)-naphthalene;

1-(4-nitrophenoxy)-2-(3-chloro-4-methoxyphenyl)-naphthalene;

1-(4-aminophenoxy)-2-(3-methoxy-4-chlorophenyl)-6-methoxynaphthalene;

1-(4-aminophenoxy)-2-(3-methoxy-4-fluorophenyl)-6-methoxynaphthalene;

1-(4-nitrophenoxy)-2-(3-methoxy-4-chlorophenyl)-6-methoxynaphthalene; and 1-(4-aminophenoxy)-2-(3-methoxy-4-fluorophenyl)-naphthalene.

The compounds of formula Ia are synthesized utilizing the compounds of formula IIb by one of two different synthetic routes, which are depicted in Scheme II.

Scheme II

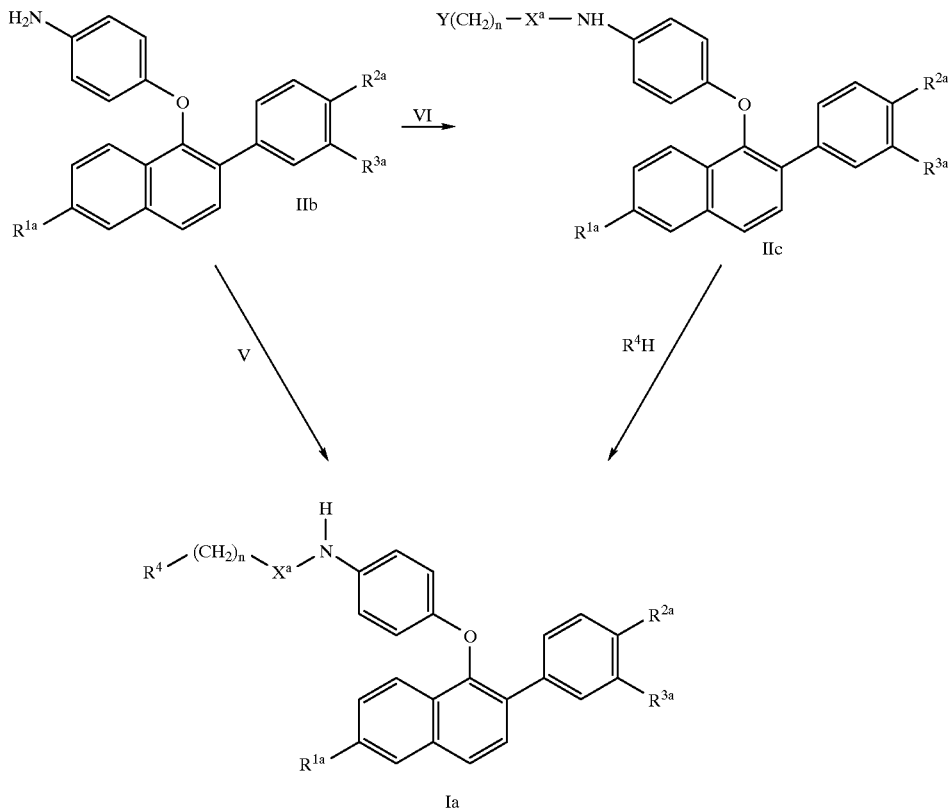

wherein:

$R^{1a}$, $R^{2a}$, $R^{3a}$, $R^4$, and n are as defined above;

$X^a$ is —CO— or —SO$_2$—; and

Y is —Cl or —Br;

or a pharmaceutically acceptable salt or solvate thereof.

In the first method of synthesis of the compounds Ia, shown in Scheme II, is the direct acylation of the amino group of IIb with a compound of formula V. Such acylations are well known in the art. A preferred method would be the reaction of a compound of formula V where Z is an acid halide, such as an acid chloride. A compound of formula IIb in an appropriate solvent, such as THF or DMF, may be coupled with a reagent, such as 2-(1-piperidine) acetyl chloride or as its hydrochloride salt, to yield a compound of formula Ia. These reactions are usually carried out at ambient temperature with an equivalent or more of an acid scavenger such as triethylamine. Compounds of formula VI are commercially available or are prepared by means well known to one of skilled in the art of organic chemistry.

$$R^4-(CH_2)_n-X^aZ \qquad V$$

wherein $R^4$, $X^a$, and n are as defined above; and Z is acid activating moiety, such as, —Cl, —Br, —N$_3$, etc.; or a salt thereof.

An alternate method of converting the compounds of formula IIb to those of Ia is by acylation of the amino function with a compound of formula VI to form the intermediate compounds of formula IIc, depicted in Scheme II. A compound of formula VI can be coupled with IIb in an appropriate solvent such as acetone, MEK, THF, or DMF at ambient temperatures. A specific illustration of this reaction is given in the preparations, below. Compounds of formula VI are either commercially available or may be easily obtained by those skilled in the art of organic chemistry.

$$Y-(CH_2)_n-X^a-Z \qquad VI$$

wherein $X^a$, Y, Z, and n are as described above.

The compounds of formula IIc are novel and useful in the synthesis of the pharmaceutically active compounds of formula I. Compounds of formula IIc would include, but not be limited to:

1-[4-N-(2-bromoacetyl)amido]phenoxy-2-(3-methoxyphenyl)-naphthalene;

1-[4-N-(2-bromoacetyl)amido]phenoxy-2-(4-methoxyphenyl)-naphthalene;

1-[4-N-(2-bromoacetyl)amido]phenoxy-2-(3,4-dimethoxyphenyl)-naphthalene;

1-[4-N-(2-chloroacetyl)amido]phenoxy-2-(3-methoxyphenyl)-naphthalene;

1-[4-N-(3-bromopropanoyl)amido]phenoxy-2-(3-methoxyphenyl)-naphthalene;

1-[4-N-(3-chloropropanoyl)amido]phenoxy-2-(3-methoxyphenyl)-naphthalene;

1-[4-N-(2-bromoacetyl)amido]phenoxy-2-(3-methoxyphenyl)-6-methoxynaphthalene;

1-[4-N-(2-bromoacetyl)amido]phenoxy-2-(4-methoxyphenyl)-6-methoxynaphthalene;

1-[4-N-(2-chloroacetyl)amido]phenoxy-2-(4-methoxyphenyl)-6-methoxynaphthalene;

1-[4-N-(3-bromopropanoyl)amido]phenoxy-2-(4-methoxyphenyl)-6-methoxynaphthalene;
1-[4-N-(2-chloroacetyl)amido]phenoxy-2-(3-methoxyphenyl)-6-methoxynaphthalene;
1-[4-N-(2-bromoacetyl)amido]phenoxy-2-(3-fluoro-4-methoxyphenyl)-6-methoxynaphthalene; and
1-[4-N-(2-chloroacetyl)amido]phenoxy-2-(3-methoxy-4-fluorophenyl)-6-methoxynaphthalene.

The compounds of formula IIc may be further converted to the compounds of formula Ib by displacement of Y with a secondary amine of $R^4$, e.g., piperidine, pyrrolidine, di-isopropylamine, and the like. This displacement reaction may be carried out in a variety of solvents such as DMF, THF, etc. at ambient temperature. In order to hasten the reaction, a molar excess of the amine ($R^4$) is employed and the reaction is generally complete within 6–24 hours. Also, a strong base is utilized to facilitate the reaction, e.g., triethylamine, $K_2CO_3$, or the like. An example of a referred method of this reaction is given in the reparations, below.

Further, the compounds of formula Ia, where $X^a$ is a carboxylic amide, may be reduced to form the compounds of formula Ib:

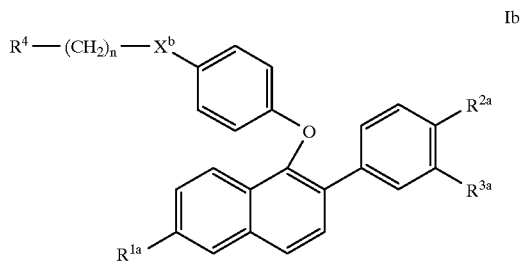

wherein $R^{1a}$, $R^{2a}$, $R^{3a}$, $R^4$, and n have their former meanings; and $X^b$ is —$CH_2NH$—; or a pharmaceutically acceptable salt or solvate thereof.

Reductions of this nature may be easily accomplished with reducing reagents such as, $LiAlH_4$, boranes, etc., in inert solvents such as THF, ether, toluene and the like.

Compounds of formula Ia or Ib, in which $R^6$, and/or $R^7$, when present, are $C_1-C_4$ alkyl, preferably methyl, are novel and are pharmaceutically active for the methods herein described. Accordingly, such compounds are encompassed by the definition herein of compounds of formula I.

Hydroxy compounds of formula I are obtained by cleaving, when present, the $R^6$ and $R^7$ hydroxy protecting groups of formula Ia and Ib compounds via well known procedures. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred $R^6$ and/or $R^7$ hydroxy protecting groups, particularly methyl, are essentially as described in Example 2 and 4, infra.

Other preferred compounds of formula I are prepared by replacing the 6, 3', and/or 4'-position hydroxy moieties, when present, with a moiety of the formula —O—CO—($C_1-C_6$ alkyl), —O—CO—Ar, or —O—$SO_2$—($C_2-C_6$ alkyl) via well known procedures. See, e.g., U.S. Pat. Nos. 5,393,763 or 5,482,949, each of which is included by reference herein.

For example, when an —O—CO($C_1-C_6$ alkyl) or —O—CO-phenyl group is desired, a mono-, di-, trihydroxy compound of formula Ia or Ib is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The present reactions are carried out at moderate temperatures, in the range from about −25° C. to about 100° C., frequently under an inert atmosphere such as nitrogen gas. However, ambient temperature is usually adequate for the reaction to run.

Acylation of a 6, 4', and/or 3'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

When a formula I compound is desired in which the 6,4', and/or 3'-position hydroxy group of a formula Ia or Ib compound is converted to a group of the formula —O—$SO_2$—($C_2-C_6$ alkyl), the mono-, di-, or trihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The hydroxy compounds also can be reacted with the appropriate sulfonic anhydride or mixed sulfonic anhydrides. Such reactions are carried out under conditions such as were explained above in the discussion of reaction with acid halides and the like.

It will be appreciated by those skilled in the art of organic chemistry that the acylation or sulfonation of the compounds of formula Ib may lead undesirable by-products, such as products of N-acylation or N-sulfonation. Such products may be minimized by using slightly less than the molar equivalent amount of sulfonating or acylating agent. Any undesired products may be removed by conventional chromatrographic techniques.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenyl acetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2- benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

PREPARATION 1

2-(4-Methoxyphenyl)-4-(3-Methoxyphenyl)butyric Acid 50.68 g (305 mmol) of 4-methoxyphenylacetic acid was dissolved in 1.4 L of THF and cooled to −70° C. under a nitrogen atmosphere. 400 mL of 1.6 M (640.5 mmol) of n-BuLi in hexane was slowly added. 72.1 g (335.5 mmol) of 2-(3-methoxyphenyl)ethylbromide in 400 mL of THF was slowly added and the reaction allowed to proceed for 1.5 hours. The reaction was allowed to warm to ambient temperature. The reaction quenched with 500 mL of 0.5 N NaOH and heated to 50° C. for one hour and cooled to ambient temperature. The reaction mixture was extracted three times with ether, the aqueous layer was acidified with 150 mL of 5N HCl and extracted twice with $CHCl_3$. The $CHCl_3$ extract was washed twice with brine, dried with $Na_2SO_4$, and evaporated to a yellow solid. This yielded 78.2 g of the title compound.

PMR: Consistent with the proposed structure. MS: m/e= 300 (M) FD EA: Calc. for $C_{18}H_{20}O_4$: C, 71.98; H, 6.71 Fd: C, 71.04; H, 6.77

PREPARATION 2

2-(4-Methoxyphenyl)-6-methoxy-1-tetralone 2.31 g(7.7 mmol) of 2-(4-methoxyphenyl)-4-(3-methoxyphenyl)butyric acid was dissolved in 30 mL of $CH_2Cl_2$ and cooled to 0° C. To this solution was added 3.4 mL (23.1 mmol) of trifluoroacetic acid, the reaction was allowed to proceed for 30 minutes. The reaction was quenched by pouring into an aqueous solution of $NaHCO_3$. The organic layer was separated, washed twice with $NaHCO_3$ solution washed twice with brine, dried with $Na_2SO_4$, and evaporated to a solid. This yielded 1.5 g of the title compound as a tan amorphous solid.

PREPARATION 3

2-(4-Methoxyphenyl)-6-methoxy-1-naphthol 8.50 g (30.14 mmol) of 2-(4-methoxyphenyl)-6-methoxy-1-tetralone was dissolved in 50 mL of isopropenyl acetate and 1 g of para-toluenesulfonic acid was added. The reaction mixture heated to reflux under a nitrogen atmosphere for six hours. The reaction mixture was allowed to cool to ambient temperature, 2,3-dichloro-5,6-dicyano-1,4-benzoquinone (DDQ), 13,7 g (60.3 mmol) was added. The reaction was refluxed for 1.5 hours, after cooling to ambient temperature, 200 mL of $CH_2Cl_2$ was added. The reaction mixture was washed four times with 200 mL portions of 0.2 N NaOH, twice with 200 mL portions of water, and the resulting solution was dried with $Na_2SO_4$ and evaporated to a solid. This yielded the intermediate phenolic acetate which was removed by dissolving the solid in 200 mL of MeOH-THF (1:1) (v/v) and added an excess amount of MeONa. An orange precipitate formed which was filtered off. The resulting filtrate was acidified with to pH 4 with 5 N HCl and diluted with 200 mL of water. The solution was extracted three times with 100 mL portions of EtOAc and organic layers combined, dried with $Na_2SO_4$, evaporated to dryness. The final product was crystallized from EtOAc-hexane, which yielded 4.24g of the title compound as a white solid.

PMR: Consistent with the proposed structure. MS: M/e= 280 (M)FD EA: Calc. for $C_{18}H_{16}O_3$: C, 77.12; H, 5.75 Fd: C, 76.83; H, 5.90

PREPARATION 4

2-(3-Methoxyphenyl)-6-methoxy-1-tetralone

In a manner similar to that used in Preparation 2, the title compound was prepared as a tan solid, mp 81–82° C.

PREPARATION 5

1-Hydroxy-2-(3-methoxyphenyl)-6-methoxynaphthalene

In a manner similar to that used in Preparation 3, the title compound was prepared as a clear oil.

PMR: ($CDCl_3$) 8.19 ppm (d, J=9.1 Hz, 1H); 7.51–6.94 ppm (m, 8H); 5.91 ppm (s, 1H); 3.94 ppm (s, 3H) MS: m/e=280 (M) FD EA: Calc. for $C_{18}H_{16}O_3$: C, 77.12; H, 5.75 Found: C, 76.91; H, 5.81.

PREPARATION 6

1-Hydroxy-2-(3-methoxyphenyl)naphthalene

In a manner analogous to Preparations 1–3, the title compound was prepared as a solid.

PMR: 8.30 ppm (m, 1H); 7.80 ppm (m, 1H); 7.57–7.45 ppm (m, 4H); 7.40 ppm (d, J=7.1 Hz, 1H); 7.35 ppm (d, J=6.0 Hz, 1H); 7.06 ppm (s, 1H0; 6.97 ppm (dd, J=6.0 Hz, 1H); 6.00 ppm (s, 1H); 3.90 ppm (s, 1H) MS: m/e=250 (M) FD EA: Calc. for $C_{17}H_{14}O_2$—0.21 mol EtOAc: C, 79.52; H, 5.93 Found: C, 79.72; H, 5.63

PREPARATION 7

1-(4-Nitrophenoxy)-2-(4-methoxyphenyl)-6-methoxynaphthalene

To a solution of 1-hydroxy-2-(4-methoxyphenyl)-6-methoxynaphthalene (3.17 g, 11.32 mmol) in 40 mL of anhydrous DMF at room temperature was added solid KO-t-Bu (1.52 g, 13.60 mmol). The dark solution was stirred for 15 min., then treated with 4-fluoronitrobenzene (3.20 g, 22.64 mmol, added as a solution in 10 mL, of DMF). The resulting mixture was warmed to 50° C. for 3 h, then cooled to room temperature. The reaction was then distributed between EtOAc/$H_2O$ (200 mL ea.). The layers were separated, and the organic was washed several times with $H_2O$. The organic was then dried ($Na_2SO_4$), and concentrated in vacuo to a yellow solid. Recrystallization from hexanes/EtOAc provided 3.68 g (81%) of 1-(4-nitro) phenoxy-2-(4-methoxyphenyl)-6-methoxynaphthalene as a yellow solid. mp 142–146° C.

PMR: (DMSO-$d_6$) d 8.10 (d, J=8.0 Hz, 2H), 7.92 (d, J=8.0 Hz, 1H), 7.63 (t (overlapping doublets, J=8.1 Hz, 2H), 7.51 (d, J=8.0 Hz, 2H), 7.48 (dd, J=2.7 Hz, 1H), 7.20 (dd, J=8.0, 2.8 Hz, 1H), 6.92 (d, J=8.0 Hz, 2H), 6.83 (d, J=8.0 Hz, 2H), 3.92 (s, 3H), 3.72 (s, 3H). MS: m/e=402 FD EA: Calcd. for $C_{24}H_{19}NO_5$: C, 71.81; H, 4.77; N, 3.49. Found: C, 72.11; H, 4.85; N, 3.70.

PREPARATION 8

1-(4-Aminophenoxy)-2-(4-methoxyphenyl)-6-methoxynaphthalene 1-(4-Nitrophenoxy)-2-(4-methoxyphenyl)-6-methoxynaphthalene (2.28 g, 5.68 mmol) was dissolved in 50 mL of 1:1 EtOH:EtOAc. To this solution was added 10% Pd/C (0.50 g). The resulting mixture was hydrogenated at 40 psi. When TLC indicated that the reduction was complete, the solution was passed through a pad of Celite to remove catalyst. The filtrate was concentrated in vacuo to an oil that solidified on standing. Isolation provided 1.68 g (81%) of 1-(4-amino)phenoxy- 2-(4-methoxyphenyl)-6-methoxynaphthalene as an off-white solid. mp 158–160° C.

PMR: (DMSO-$d_6$) d 7.79 (d, J=8.0 Hz, 1H), 7.72 (d, J=8.1 Hz, 1H), 7.58 (d, J=8.1 Hz, 1H), 7.51 (d, J=8.0 Hz, 2H), 7.40 (d, J=2.8 Hz, 1H), 7.13 (dd, J=8.0, 2.8 Hz, 1H), 6.92 (d, J=8.0 Hz, 2H), 6.38 (s, 4H). MS: m/e=371 FD EA: Calcd. for $C_{24}H_{21}NO_3$: C, 77.61; H, 5.70; N, 3.77. Found: C, 77.79; H, 5.86; N, 3.77.

PREPARATION 9

1-[4-(2-Chloroacetylamido)phenoxy]-2-(4-methoxyphenyl)-6-methoxynaphthalene

A solution was prepared of 1.03 g (2.7 mmol) of 1-(4-aminophenoxy)-2-(4-methoxyphenyl)-6-methoxynaphthalene and 745 mg (5.4 mmol) of $K_2CO_3$ in 15 mL of acetone. To this solution was slowly added 362 mg (0.26 mL, 5.4 mmol) of 2-chloroacetylchloride. The reaction was allowed to proceed at ambient temperature under a nitrogen atmosphere for one hour. The solvent was evaporated and residue suspended in 50 mL of water. The aqueous suspension was extracted three times with 25 mL portions of EtOAc. The combined EtOAc extracts was washed with water, brine, dried with $Na_2SO_4$, and evaporated to dryness. This yielded 1.2 g of the title compound as a tan amorphous solid.

PMR: Consistent with the proposed structure. MS: m/e= 446,448 (M) FD EA: Calc. for $C_{26}H_{22}ClNO_4$: C, 69.72; H, 4.95; N, 3.13 Found: C, 70.00; H, 4.72; N, 3.20.

EXAMPLE 1

1-[4-[2-(1-Piperidinyl)acetylamido]phenoxy]-2-(4-methoxyphenyl)-6-methoxynaphthalene A solution was prepared of 1.2 g (2.68 mmol) of 1-[4-(2-chloroacetylamido)phenoxy]-2-(4-methoxyphenyl)-6-methoxynaphthalene and 980 mg (8.05 mmol) of piperidine hydrochloride in 20 mL of DMF. To this solution was added 1.63 g (2.25 mL, 16.2 mmol) of triethylamine. The reaction was allowed to proceed at ambient temperature under a nitrogen atmosphere for forty-eight hours. The reaction mixture was poured into 50 mL of water and was extracted three times with 25 mL portions of $CH_2Cl_2$. The combined $CH_2Cl_2$ extracts was washed with water, brine, dried with $Na_2SO_4$, and evaporated to dryness. The crude product was crystallized from $CH_2Cl_2$—EtOAc. This yielded 609 mg of the title compound as a white powder, mp: 211–214° C.

PMR: Consistent with the proposed structure. MS: m/e= 496 (M) FD EA: Calc. for $C_{31}H_{32}N_2O_4$: C, 74.98; H, 6.50; N, 5.64 Found: C, 75.17; H, 6.53; N, 5.69.

EXAMPLE 2

1-[4-[2-(1-Piperidinyl)acetylamido]phenoxy-2-(4-hydroxyphenyl)-6-hydroxynaphthalene Hydrochloride A solution was prepared of 609 mg (1.23 mmol) of 1-[4-[2-(1-piperidinyl)acetylamido]phenoxy]-2-(4-methoxyphenyl)-6-methoxynaphthalene in 25 mL of $CH_2Cl_2$, which was cooled to 10° C. To this solution was added 925 mg (0.35 mL, 3.7 mmol) of $BBr_3$. The reaction was allowed to proceed at −8° C. under a nitrogen atmosphere for two hours. The reaction was quenched by pouring into 50 mL of aqueous $NaHCO_3$. The aqueous solution was extracted with EtOAc. The EtOAc extracted was washed twice with brine, dried with $Na_2SO_4$, and evaporated to dryness. This yielded 611 mg of the title compound as its free base (PMR: Consistent with the proposed structure). The base was dissolved in EtOAc and precipitated by addition of $Et_2O$-saturated with HCl. The white precipitate was collected and dried. This yielded 520 mg of the title compound as a white amorphous powder, mp: 163–166° C.

PMR: Consistent with the proposed structure. MS: m/e= 468 (M-HCl) FD EA: Calc. for $C_{29}H_{28}N_2O_4$—HCl: C, 68.97; H, 5.79; N, 5.55 Found: C, 69.17; H, 5.75; N, 5.29.

EXAMPLE 3

1-[4-[2-(1-Piperidinyl)ethylamino]phenoxy]-2-(4-methoxyphenyl)-6-methoxynaphthalene Hydrochloride A suspension of 460 mg (12 mmol) of $LiALH_4$ in 10 mL of anhydrous THF was prepared. To this suspension was added 1.19 g (2.4 mmol) of 1-[4-[2-(1-piperidinyl) acetylamido]phenoxy]-2-(4-methoxyphenyl)-6-methoxynaphthalene in 70 mL of THF. The reaction was allowed to proceed at reflux temperature under a nitrogen atmosphere for sixteen hours. The reaction mixture was cooled to 0° C. and water was added to quench the reaction. The reaction mixture was extracted three times with EtOAc. The combined EtOAc extracts was washed three times with water, brine, dried with $Na_2SO_4$, and evaporated to dryness. The product was purified by chromatography on a silica gel column eluted with a linear gradient beginning with $CHCl_3$ and ending with $CHCl_3$—MeOH (98:2) (v/v). The desired fractions were determined by TLC, combined, and evaporated to dryness. This yielded 970 mg of the title compound as its free base. The base was dissolved in 25 mL of EtOAc and Et$_2$O—HCl was added. A precipitate formed, which filtered and dried. This yielded 948 mg of the title compound as a tan, amorphous solid, mp: 218–221° C.

PMR: Consistent with the proposed structure. MS: m/e-482 (M-HCl) FD EA: Calc. for $C_{31}H_{34}N_2O_3$—HCl: C, 71.73; H, 6.80; N, 5.40 Found: C, 71.95; H, 6.93; N, 5.52.

EXAMPLE 4

1-[4-[2-(1-Piperidinyl)ethylamino]phenoxy]-2-(4-hydroxyphenyl)-6-hydroxynaphthalene A solution was prepared of 200 mg (0.38 mmol) of 1-[4-[2-(1-piperidinyl)ethylamino]phenoxy]-2-(4-methoxyphenyl)-6-methoxynaphthalene hydrochloride in 10 mL of CH$_2$Cl$_2$ and cooled to 0° C. under a nitrogen atmosphere. To this solution was added 480 mg (0.18 mL, 1.93 mmol) of BBr$_3$ and the reaction was allowed to proceed for thirty minutes. The reaction was quenched by the addition of a saturated, aqueous solution of NaHCO$_3$. The aqueous solution was extracted thrice with EtOAc. The combined EtOAc extract was dried with Na$_2$SO$_4$ and evaporated to dryness. This yielded 161 mg of the title compound as a white amorphous powder.

PMR: Consistent with the proposed structure. MS: m/e= 454 (M+) FD EA: Calc. for $C_{29}H_{30}N_2O_3$: C, 76.62; H, 6.65; N, 6.16 Found: C, 76.67; H, 6.82; N, 6.14.

We claim:

1. A compound of formula I

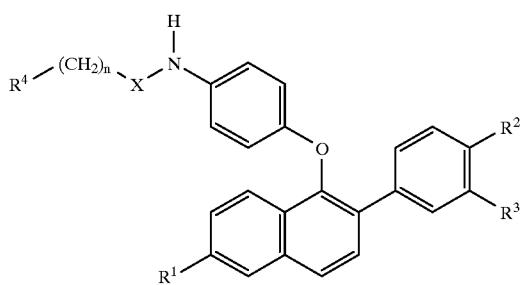

or a pharmaceutically acceptable salt thereof wherein
n is 1, 2 or 3;
$R^1$ is selected from the group consisting of
hydrogen,
hydroxyl,
alkoxy of one to four carbon atoms,
alkoxycarbonyl of two to seven carbon atoms,
—OSO$_2$(C$_1$–C$_6$ alkyl), and
—OCOAr where Ar is selected from the group consisting of
unsubstituted phenyl, and
phenyl substituted with one or more substituents independently selected from the group consisting of
halo,
nitro,
trifluoromethyl,
methyl, and
methoxy;
$R^2$ and $R^3$ are independently selected from the group consisting of
hydrogen,
hydroxyl,
halo,
alkoxy of one to four carbon atoms,
alkoxycarbonyl of two to seven carbon atoms,
—OSO$_2$(C$_2$–C$_6$ alkyl), and
—OCOAr where Ar is selected from the group consisting of
unsubstituted phenyl, and
phenyl substituted with one or more substituents independently selected from the group consisting of
halo,
nitro,
trifluoromethyl,
methyl, and
methoxy;
$R^4$ is selected from the group consisting of
1-piperidinyl,
1-pyrrolidinyl,
methyl-1-pyrrolidinyl,
dimethyl-1-pyrrolidino,
4-morpholino,
dimethylamino,
diethylamino,
diisopropylamino, and
1-hexamethyleneimino; and
X is absent or is selected from the group consisting of
—C(O)— and —SO$_2$—.

2. A compound according to claim 1 wherein X is absent, or a pharmaceutically acceptable salt thereof.

3. A compound according to claim 1 wherein X is —C(O)— or a pharmaceutically acceptable salt or solvate thereof.

4. A compound according to claim 1 wherein X is —(SO$_2$)— or a pharmaceutically acceptable salt or solvate thereof.

5. A compound according to claim 1 wherein $R^1$ and $R^2$ are hydroxy and $R^3$ is hydrogen.

6. A compound according to claim 1 wherein $R^4$ is piperidinyl.

7. A compound according to claim 2 wherein n is 1.

8. A compound according to claim 1 selected from the group consisting of
1-[4-[2-(1-piperidinyl)ethylamino]phenoxy]-2-(4-hydroxyphenyl)-6-hydroxynaphthalene;
1-[4-[2-(1-piperidinyl)ethylamino]phenoxy]-2-(4-methoxyphenyl)-6-methoxynaphthalene;
1-[4-[2-(1-piperidinyl)ethylamino]phenoxy]-2-(4-hydroxyphenyl)-6-methoxynaphthalene;
1-[4-[2-(1-piperidinyl)ethylamino]phenoxy]-2-(4-methoxyphenyl)-6-hydroxynaphthalene;
1-[4-[2-(1-pyrolidinyl)ethylamino]phenoxy]-2-(4-hydroxyphenyl)-6-hydroxynaphthalene;
1-[4-[3-(1-piperidinyl)propylamino]phenoxy]-2-(4-hydroxyphenyl)-6-hydroxynaphthalene;
1-[4-[2-(1-piperidinyl)ethylamino]phenoxy]-2-(3-hydroxyphenyl)-6-hydroxynaphthalene;
1-[4-[2-(1-piperidinyl)ethylamino]phenoxy]-2-(3-methoxyphenyl)-6-hydroxynaphthalene;
1-[4-[2-(1-piperidinyl)ethylamino]phenoxy]-2-(4-hydroxyphenyl)naphthalene;
1-[4-[2-(1-piperidinyl)ethylamino]phenoxy]-2-(4-methoxyphenyl)naphthalene;
1-[4-[2-(1-piperidinyl)ethylamino]phenoxy]-2-(3-hydroxyphenyl)naphthalene;
1-[4-[2-(1-piperidinyl)ethylamino]phenoxy]-2-(3-methoxyphenylnaphthalene;

1-[4-[2-(1-piperidinyl)ethylamino]phenoxy]-2-(4-acetyloxyphenyl)-6-hydroxynaphthalene;
1-[4-[2-(1-piperidinyl)ethylamino]phenoxy]-2-(4-hydroxyphenyl)-6-benzoyloxynaphthalene;
1-[4-[2-(1-piperidinyl)acetylamido]phenoxy]-2-(4-hydroxyphenyl)-6-hydroxynaphthalene;
1-[4-[2-(1-pyrolidinyl)acetylamido]phenoxy]-2-(4-hydroxyphenyl)-6-hydroxynaphthalene;
1-[4-[2-(1-piperidinyl)acetylamido]phenoxy]-2-(4-methoxyphenyl)-6-methoxynaphthalene;
1-[4-[2-(1-piperidinyl)acetylamido]phenoxy]-2-(3-hydroxyphenyl)-6-hydroxynaphthalene;
1-[4-[2-(1-piperidinyl)acetylamido]phenoxy]-2-(4-hydroxyphenyl)naphthalene;
1-[4-[2-(1-piperidinyl)acetylamido]phenoxy]-2-(4-methoxyphenyl)-6-hydroxynaphthalene;
1-[4-[3-(1-piperidinyl)propanoylamido]phenoxy]-2-(4-hydroxyphenyl)-6-hydroxynaphthalene;
1-[4-[(1-piperidinyl)methylsulfonoylamido]phenoxy]-2-(4-hydroxyphenyl)-6-hydroxynaphthalene; and
1-[4-[2-(1-piperidinyl)ethylsulfonoylamido]phenoxy]-2-(4-hydroxyphenyl)-6-hydroxynaphthalene; or
a pharmaceutically acceptable salt thereof.

9. A compound of formula II

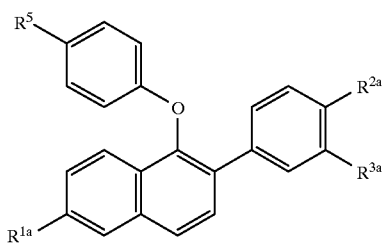

II or a pharmaceutically acceptable salt or solvate thereof useful in the preparation of a compound of claim 1 wherein
R$^{1a}$ is selected from the group consisting of hydrogen, and —OR$^6$ in which R$^6$ is a hydroxy protecting group;
R$^{2a}$ and R$^{3a}$ are independently selected from the group consisting of
hydrogen,
halo, and
—OR$^6$;
R$^5$ is selected from the group consisting of
—NO$_2$,
—NH$_2$, and
Y—(CH$_2$)$_n$—X$^a$—NH— where n is 1, 2 or 3, Y is chloro or bromo; and X$^a$ is absent or is —CO— or —SO$_2$—.

10. A compound according to claim 9 wherein R$^6$ and R$^7$ each are methyl.

11. A compound according to claim 10 wherein R$^5$ is —NO$_2$.

12. A compound according to claim 10 wherein R$^5$ is —NH$_2$.

13. A compound according to claim 10 wherein R$^5$ is 2-(1-piperidnyl)acetylamido.

14. A pharmaceutical composition comprising an effective amount of a compound according to claim 1, or a pharmaceutically acceptable salt or solvate thereof, in combination with a pharmaceutically acceptable carrier, diluent, or excipient.

15. A method of treating a human suffering from estrogen deprivation comprising administering to a patient in need of such treatment an effective amount of a compound of claim 1.

16. A method according to claim 15, wherein the estrogen deprivation is due to ovariectomy.

17. A method according to claim 15, wherein the estrogen deprivation is due to menopause.

18. A method according to claim 15, wherein the estrogen deprivation manifests in a pathology of osteoporosis.

19. A method according to claim 15, wherein the estrogen deprivation manifests in a pathology of cardiovascular disease.

20. A method according to claim 19, wherein the cardiovascular disease is hyperlipidemia.

21. A method according to claim 19, wherein the estrogen deprivation manifests a pathology of aortal smooth muscle cell proliferation.

22. A method of treating estrogen dependent cancer comprising administering to a patient in need of such treatment an effective amount of a compound of claim 1.

23. A method of treating endometriosis comprising administering to a patient in need of such treatment an effective amount of a compound of claim 1.

24. A method of treating uterine fibroid disease comprising administering to a patient in need of such treatment an effective amount of a compound of claim 1.

* * * * *